(12) United States Patent
Hatta et al.

(10) Patent No.: US 9,662,244 B2
(45) Date of Patent: May 30, 2017

(54) MEDICAL TREATMENT DEVICE

(71) Applicant: Terumo Kabushiki Kaisha, Tokyo (JP)

(72) Inventors: Tomonori Hatta, Hadano (JP); Makoto Narita, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 141 days.

(21) Appl. No.: 14/534,457

(22) Filed: Nov. 6, 2014

(65) Prior Publication Data

US 2015/0126919 A1 May 7, 2015

(30) Foreign Application Priority Data

Nov. 7, 2013 (JP) .................... 2013-231504

(51) Int. Cl.
*A61B 5/00* (2006.01)
*A61F 9/007* (2006.01)

(52) U.S. Cl.
CPC ................ *A61F 9/00781* (2013.01)

(58) Field of Classification Search
CPC .................................. A61F 9/00781
See application file for complete search history.

(56) References Cited

U.S. PATENT DOCUMENTS

| 4,402,681 | A | * | 9/1983 | Haas ................ A61F 9/00781 604/175 |
| 5,626,559 | A | * | 5/1997 | Solomon ........... A61F 9/00781 604/289 |
| 5,743,868 | A | | 4/1998 | Brown et al. |
| 2012/0089072 | A1 | * | 4/2012 | Cunningham, Jr. A61F 9/00781 604/9 |

* cited by examiner

*Primary Examiner* — Leslie Deak
(74) *Attorney, Agent, or Firm* — Foley & Lardner LLP

(57) ABSTRACT

A medical treatment device for treating glaucoma includes a spherical portion formed in a partially spherical shape configured to align with the curve of an eyeball; and at least one puncture portion protruding from a concave side of the spherical portion.

20 Claims, 9 Drawing Sheets

MEDICAL TREATMENT DEVICE

CROSS-REFERENCE TO RELATED APPLICATION

This application claims priority to Japanese Patent Application No. 2013-231504, filed on Nov. 7, 2013, which is hereby incorporated by reference in its entirety.

BACKGROUND

Field of the Invention

The present disclosure relates to a medical treatment device.

Description of Related Art

A medical treatment device for treating glaucoma is conventionally known (see, for example, U.S. Pat. No. 5,743,868).

The medical treatment device disclosed in U.S. Pat. No. 5,743,868 includes a pipe member, a tubular member, and a pushing out member. The pipe member is cut obliquely at a distal end thereof. The tubular member has, provided at one end thereof, a flange portion that is capable of being absorbed by the eyeball and accommodates the pipe member therein. The pushing out member is provided for back and forth movement in the tubular member and used to push out the pipe member. When the medical treatment device is used to treat a patient, the tubular member is absorbed at the flange portion thereof on a surface of the eyeball. In this state, the pipe member is pushed out by the pushing out member so as to penetrate the cornea until the distal end of the pipe member is positioned in the anterior chamber. Thereafter, the tubular member and the pushing out member are removed while the pipe member is indwelled so that the aqueous humor in the anterior chamber is discharged through the pipe member. Consequently, a high intraocular pressure by the glaucoma decreases.

However, such a conventional medical treatment device as disclosed in U.S. Pat. No. 5,743,868 has a problem in that a heavy burden is placed on a patient because a highly invasive technique is involved in treatment of the patient.

SUMMARY OF THE INVENTION

One objective of certain embodiments of the present invention is to provide a medical treatment device which can reduce the burden to be placed on a patient upon treatment of glaucoma.

A medical treatment device for treating glaucoma according to certain embodiments of the present invention includes a spherical portion formed in a spherical shape along the eyeball, and at least one puncture portion provided at a given position of the spherical portion on an eyeball side so as to project from the spherical portion and having a given length.

Because the puncture portion is provided on the eyeball side of the spherical portion, the medical treatment device can be mounted on the eyeball similarly to a contact lens, and the burden on the patient upon treatment of the glaucoma can be reduced.

In one aspect, the medical treatment device is configured such that the puncture portion has a groove formed thereon extending in a projection direction.

Because the puncture portion has the groove extending in the projection direction, the aqueous humor can be discharged along the groove. Consequently, the discharging efficiency of the aqueous humor can be improved.

In one aspect, the medical treatment device is configured such that the puncture portion has a through-hole formed therein extending through the puncture portion and the spherical portion.

Because the through-hole extending through the puncture portion and the spherical portion is provided, the aqueous humor can be discharged from through the through-hole, and the discharging efficiency of the aqueous humor can be improved.

Further, because the aqueous humor is discharged to an outer surface of the medical treatment device through the through-hole, the outer surface of the medical treatment device can be kept in a wet state.

In one aspect, the medical treatment device is configured such that a plurality of puncture portions are provided that individually have an opening, and the spherical portion and the puncture portions have a communication passage formed therein so as to communicate the openings of the puncture portions with each other.

Because the aqueous humor discharged once can be returned to the sclera through the communication passage, the eyeball can be prevented from being inflected by emissions.

In one aspect, the medical treatment device is configured such that the spherical portion and the puncture portion are formed from a material having biodegradability.

Because the spherical portion and the puncture portion are formed from a material having biodegradability, a stimulus to the eyeball can be suppressed. Therefore, the medical treatment device can be left mounted for a long period of time on the eyeball, and removal of the medical treatment device from the eyeball can be carried out readily.

In one aspect, the medical treatment device is configured such that the spherical portion has an opening formed at a central portion thereof.

Because the spherical portion has the opening formed at a central portion thereof, the central portion of the spherical portion can be prevented from being soiled by emissions discharged along the puncture portion.

Further, because a surface of the eyeball can be exposed through the opening, the oxygen permeability of the spherical portion can be improved.

In one aspect, the medical treatment device is configured such that it further includes a puncturing member having a projection for causing the puncture portion to puncture the eyeball, and such that the spherical portion and the puncture portion have an accommodation hole extending in the puncture portion through the spherical portion and configured to accommodate the projection of the puncturing member therein. The puncturing member being provided for separation from the spherical portion and the puncture portion.

Because the puncturing member is provided, the spherical portion and the puncture portion can be formed from a soft material, and an uncomfortable feeling of a patient while the medical treatment device is indwelled can be moderated.

In one aspect, the medical treatment device is configured such that the puncture portion is provided at a position corresponding to the cornea when the medical treatment device is mounted on the eyeball.

Because the puncture portion is provided at the position of the cornea, the aqueous humor can be discharged efficiently.

In one aspect, the medical treatment device is configured such that the puncture portion has a length sufficient to allow the puncture portion to reach an angle, or to extend through the iris when the medical treatment device is mounted on the eyeball.

Because the puncture portion has such a length that it can reach the angle or penetrate the iris, the aqueous humor can be discharged efficiently.

In one aspect, the medical treatment device is configured such that a plurality of puncture portions are provided, and the plurality of puncture portions include a first puncture portion having a length sufficient to allow the puncture portion to reach the angle or to extend through the iris when the medical treatment device is mounted on the eyeball and a second puncture portion having a length sufficient to allow the second puncture portion to reach the vitreous body.

Because the first puncture portion has a length sufficient to allow the puncture portion to reach the angle or to extend through the iris, the aqueous humor can be discharged efficiently. Further, when complications of glaucoma and age-related macular degeneration occur, if anti-vascular endothelial growth factor (VEGF) agents necessary for treatment of the age-related macular degeneration are instilled in a state in which the medical treatment device is mounted on the eyeball, then the anti-vascular endothelial growth factor agents can be administered into the vitreous body through the second puncture portion.

In one aspect, the medical treatment device is configured such that the second puncture portion has anti-vascular endothelial growth factor agents applied thereto. If the medical treatment device is mounted on the eyeball, then the anti-vascular endothelial growth factor agents applied to the surface of the second puncture portion in advance can be administered into the vitreous body.

In one aspect, the medical treatment device is configured such that a gel-like material is applied to an outer edge portion of the spherical portion.

Because a gel-like material is applied to the outer edge portion of the spherical portion, the spherical portion is less likely to move, and the medical treatment device can be prevented from being displaced with respect to the eyeball.

DETAILED DESCRIPTION

Figure 1A:
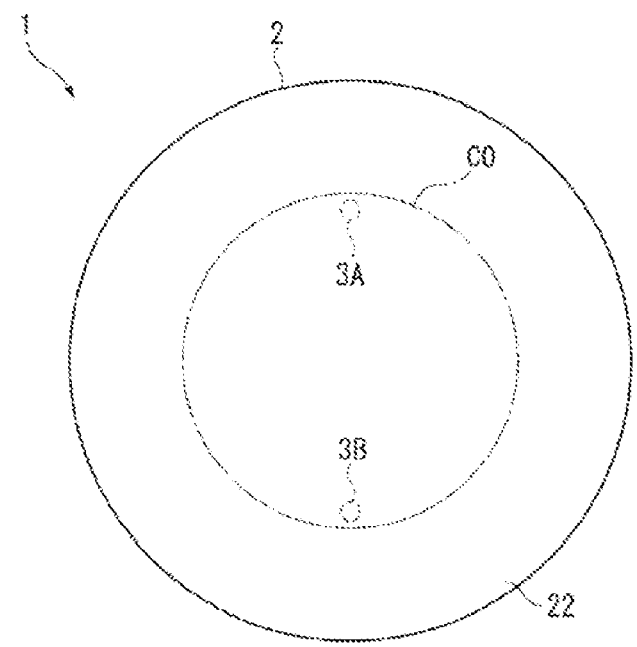
FIGS. 1A and 1B are a plan view and a side elevational view, respectively, of a medical treatment device according to a first embodiment of the present invention.

In the following, embodiments of the present invention are described with reference to the drawings.

It is to be noted that the dimensional ratio in the drawings is sometimes different from an actual dimensional ratio for the convenience of illustration.

Further, in the second and succeeding embodiments, like components and components having like functions to those described in connection with the first embodiment are denoted by like reference characters applied in the first embodiment and description of them is omitted or simplified herein.

First Embodiment

Figure 1B:
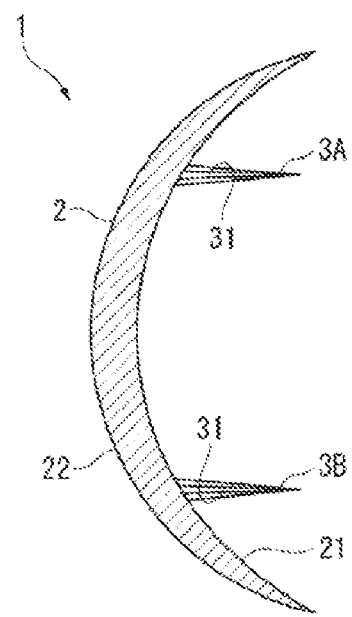
Figure 2:
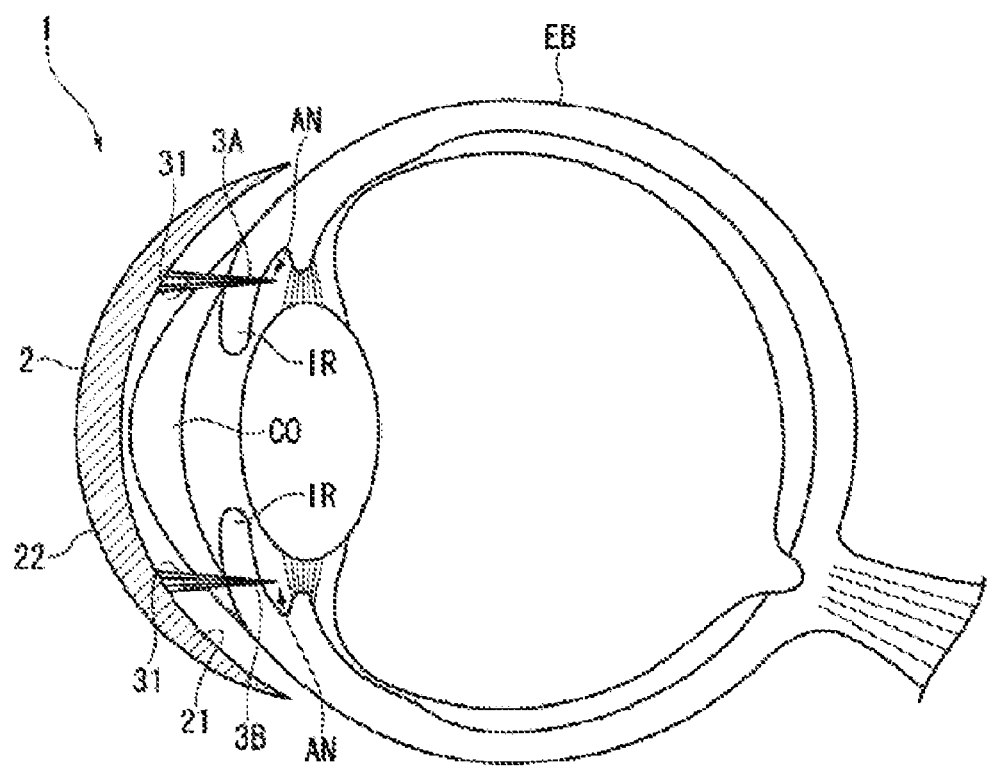
FIG. 2 is a side elevational view illustrating an example of use of the medical treatment device of FIGS. 1A and 1B.

Referring first to FIGS. 1A, 1B, and 2, a medical treatment device 1 includes a spherical portion 2 formed in a spherical shape along an eyeball EB, and at least one puncture portion, in the embodiment depicted, two puncture portions 3A and 3B. The puncture portions 3A and 3B are provided at predetermined positions of the spherical portion 2 on the eyeball EB side so as to project from the spherical portion 2 and have a predetermined length. The spherical portion 2 and the puncture portions 3A and 3B of the medical treatment device 1 are formed from a material which is transparent and biodegradable such as, for example, an oxygen-permeable (RGP: Rigid Gas Permeable) lens material or polymethyl methacrylate which are used for general hard contact lenses, or a hydrous material such as polyhydroxyethylmethacrylate, a non-hydrous material such as acrylic elastomer, or a high oxygen-permeable material such as silicone hydrogel, which are used for general soft contact lenses. The spherical portion 2 and the puncture portions 3A and 3B are formed as a unitary member.

The spherical portion 2 has a shape similar to that of a contact lens and is formed in a circular shape as viewed in plan and in a shape recessed at a central portion thereof as viewed in side elevation. An inner side face 21 of the spherical portion 2, namely, a face of the spherical portion 2 on the eyeball EB side, has a spherical face along the eyeball EB. A gel-like material such as an acrylic resin having low skin irritation is applied to an outer edge portion of the inner side face 21 of the spherical portion 2. It is to be noted that, although it is depicted in FIG. 2 that a gap exists between the spherical portion 2 and eyeball EB for the convenience of illustration, when the medical treatment device 1 is mounted on the eyeball EB, the spherical portion 2 contacts more closely with the eyeball EB.

The puncture portions 3A and 3B are microneedles and have a shape of a needle projecting from the inner face of the spherical portion 2. The puncture portions 3A and 3B are provided at positions indicated by alternate long and short dash lines in FIG. 1A and of a cornea CO depicted in FIG. 2, preferably at positions of iris IR. The puncture portions 3A and 3B have a length with which they penetrate the cornea CO and reach an angle AN. Where the puncture portions 3A and 3B are provided at positions of the iris IR, they are more advantageous for the assurance of the field of view. Further, the puncture portions 3A and 3B have a diameter of, for example, approximately 10 to 200 microns and preferably are minimally invasive. Grooves 31 are formed on a side face of the puncture portions 3A and 3B so as to extend in a projection direction of the puncture portions 3A and 3B from a distal end of the puncture portions 3A and 3B to the inner side face 21 of the spherical portion 2.

When the medical treatment device 1 having the configuration described above is mounted on the eyeball EB as depicted in FIG. 2, the puncture portions 3A and 3B puncture the cornea CO until the distal ends of the puncture portions 3A and 3B reach the angle AN. Therefore, the aqueous humor staying at the angle AN can be discharged to the outside of the puncture portions 3A and 3B along the puncture portions 3A and 3B, and the intraocular pressure which has been raised by the glaucoma can be decreased. Here, because the grooves 31 are formed on the puncture portions 3A and 3B from the distal end of the puncture portions 3A and 3B toward the inner face of the spherical portion 2, the aqueous humor can be discharged along the grooves 31. Consequently, the discharging efficiency of the aqueous humor can be enhanced.

With the present embodiment having the configuration described above, the following effects are achieved.

In particular, because the puncture portions 3A and 3B are provided on the eyeball EB side of the spherical portion 2, the medical treatment device 1 can be mounted on the eyeball EB similarly to a contact lens, and the burden on the patient upon treatment of the glaucoma can be reduced.

Further, because the puncture portions 3A and 3B have the grooves 31 extending in the projection direction, the aqueous humor can be discharged along the grooves 31. Consequently, the discharging efficiency of the aqueous humor can be improved.

Further, because the spherical portion 2 and the puncture portions 3A and 3B are formed from a material having biodegradability, a stimulus to the eyeball EB can be suppressed. Therefore, the medical treatment device 1 can be left mounted for a long period of time on the eyeball EB, and removal of the medical treatment device 1 from the eyeball EB can be carried out readily.

Further, because the puncture portions 3A and 3B are provided at positions of the cornea CO, the aqueous humor can be discharged efficiently.

Further, because the puncture portions 3A and 3B have such a length that they can reach the angle AN or penetrate the iris IR, the aqueous humor can be discharged efficiently.

Furthermore, because a gel-like material is applied to an outer edge portion of the spherical portion 2, the spherical portion 2 is less likely to move, and the medical treatment device 1 can be prevented from being displaced with respect to the eyeball EB.

Second Embodiment

Figure 3A:
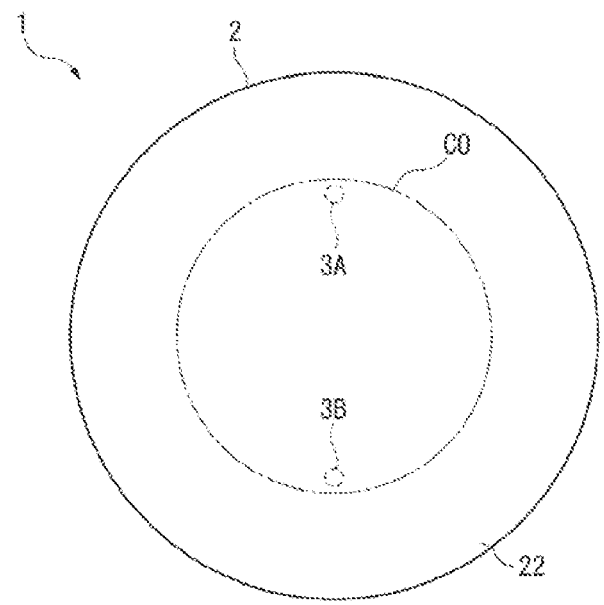
FIGS. 3A and 3B are a plan view and a side elevational view, respectively, of a medical treatment device according to a second embodiment of the present invention.
Figure 3B:
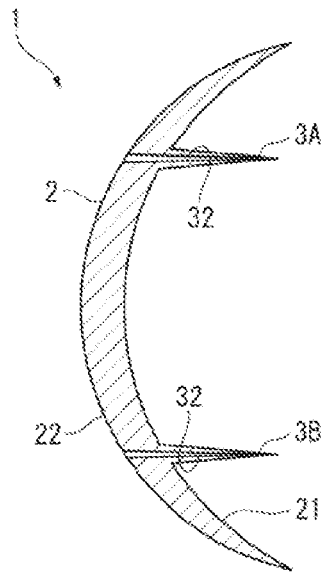

A medical treatment device 1 according to a second embodiment of the present invention is different from that of the first embodiment in that the puncture portions 3A and 3B have a through-hole 32 extending through the puncture portions 3A and 3B and the spherical portion 2 as depicted in FIGS. 3A and 3B.

The through-hole 32 is formed to extend in the projection direction of the puncture portions 3A and 3B. The through-hole 32 is open at one end thereof to the distal end of the puncture portions 3A and 3B and open at the other end thereof to an outer side face 22 of the spherical portion 2.

With the present embodiment, the following effect is achieved in addition to the effects of the first embodiment.

In particular, because the aqueous humor is discharged to the outer surface of the medical treatment device 1 through the through-holes 32, the outer surface of the medical treatment device 1 can be kept in a wet state.

Third Embodiment

Figure 4A:
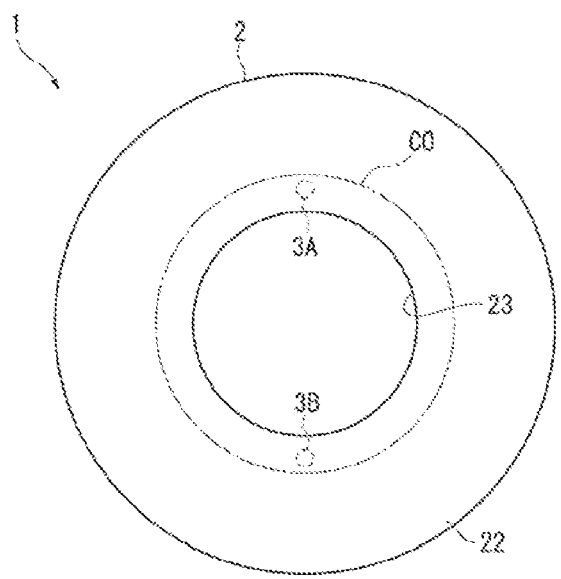
FIGS. 4A and 4B are a plan view and a side elevational view, respectively, of a medical treatment device according to a third embodiment of the present invention.
Figure 4B:
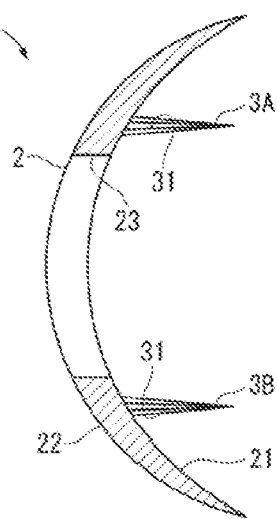

A medical treatment device 1 according to a third embodiment of the present invention is different from that of the first embodiment in that the spherical portion 2 has an opening 23 at a central portion thereof as depicted in FIGS. 4A and 4B.

With the present embodiment, the following effects are achieved in addition to the effects of the first embodiment.

In particular, because the spherical portion 2 has the opening 23, the central portion of the spherical portion 2 can be prevented from being soiled by emissions discharged along the puncture portions 3A and 3B.

Further, because the surface of the eyeball EB can be exposed through the opening 23, the oxygen permeability of the spherical portion 2 can be improved.

Fourth Embodiment

Figure 5A:
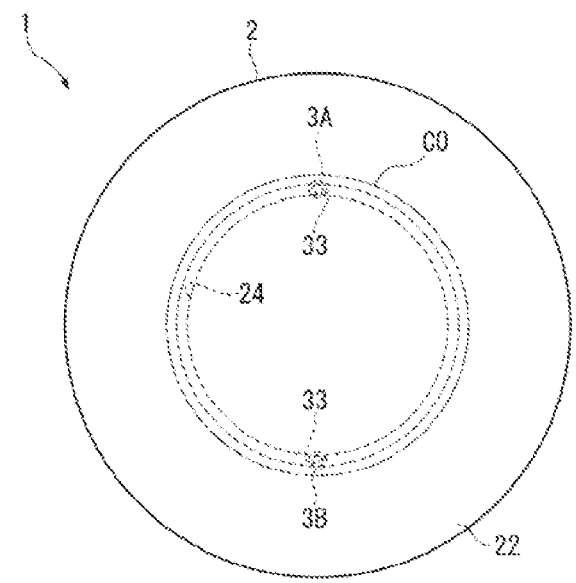
FIGS. 5A and 5B are a plan view and a side elevational view, respectively, of a medical treatment device according to a fourth embodiment of the present invention.
Figure 5B:
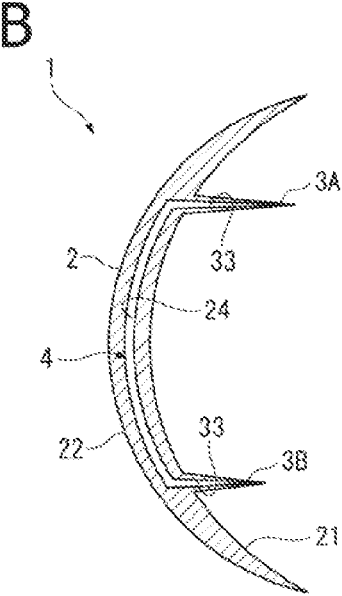
Figure 6:
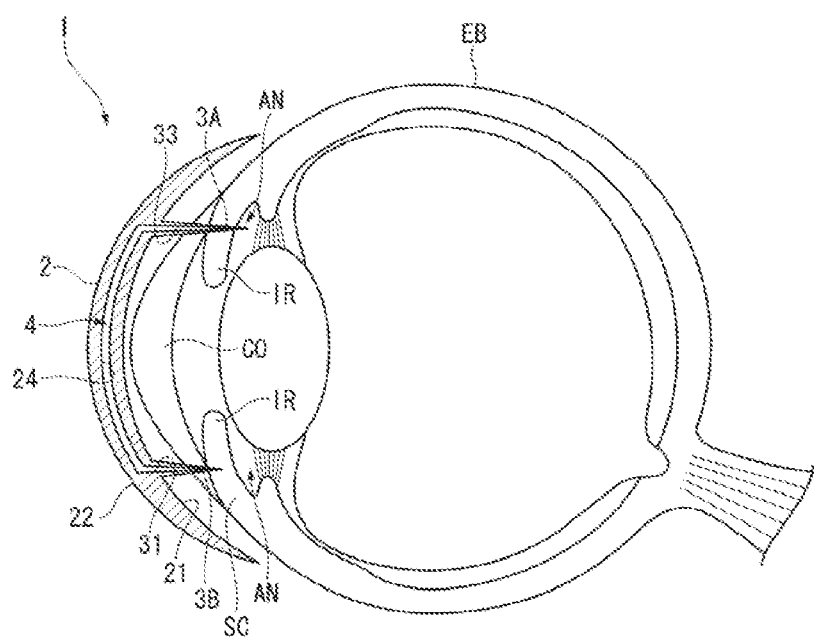
FIG. 6 is a side elevational view illustrating an example of use of the medical treatment device of FIGS. 5A and 5B.

A medical treatment device 1 according to a fourth embodiment of the present invention is different from that of the first embodiment in that the spherical portion 2 and the puncture portions 3A and 3B are different in configuration and that a communication passage 4 is provided in the spherical portion 2 and the puncture portions 3A and 3B as depicted in FIGS. 5A, 5B, and 6.

An annular passage 24 is provided in the spherical portion 2 and formed concentrically with the spherical portion 2 as viewed in plan.

The puncture portions 3A and 3B individually have an opening at the distal end thereof and has a passage 33 provided therein for connecting the opening and the annular passage 24. Here, the puncture portion 3A has such a length that it extends through the cornea CO and reaches the angle AN when the medical treatment device 1 is mounted on the eyeball EB as depicted in FIG. 6 while the other puncture portion 3B has such a length that it extends through the cornea CO and reaches a sclera SC.

The communication passage 4 is configured from the annular passage 24 of the spherical portion 2 and the passages 33 of the puncture portions 3A and 3B and communicates the openings of the puncture portion 3A and the puncture portion 3B with each other.

With the present embodiment, the following effect is achieved in addition to the effects of the first embodiment.

In particular, because the aqueous humor discharged once can be returned to the sclera SC through the communication passage 4, the eyeball EB can be prevented from being inflected by emissions.

Fifth Embodiment

Figure 7:
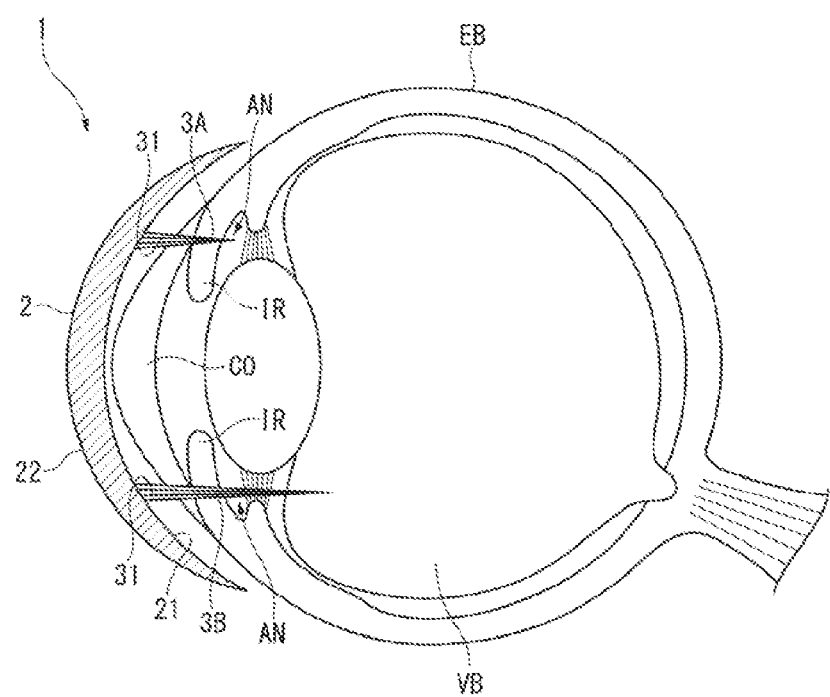
FIG. 7 is a side elevational view of a medical treatment device according to a fifth embodiment of the present invention.

A medical treatment device 1 according to a fifth embodiment of the present invention is different from that of the first embodiment in configuration of the puncture portion 3B as depicted in FIG. 7.

The medical treatment device 1 includes the spherical portion 2, a puncture portion 3A as a first puncture portion, and a puncture portion 3B as a second puncture portion having such a length that it reaches a vitreous body VB when the medical treatment device 1 is mounted on the eyeball EB.

With the present embodiment, the following effects are achieved in addition to the effects of the first embodiment.

In particular, when complications of glaucoma and age-related macular degeneration occur, if anti-vascular endothelial growth factor agents necessary for treatment of the age-related macular degeneration are instilled in a state in which the medical treatment device 1 is mounted on the eyeball EB, then the anti-vascular endothelial growth factor agents can be administered into the vitreous body VB through the puncture portion 3B. It is to be noted that, because the internal pressure of the aqueous humor is high, the anti-vascular endothelial growth factor agents do not enter the eye chamber through the puncture portion 3A.

Further, if anti-vascular endothelial growth factor agents are applied to the surface of the puncture portion 3B in advance, then if the medical treatment device 1 is mounted on the eyeball EB, then the anti-vascular endothelial growth factor agents applied to the surface of the puncture portion 3B in advance can be administered into the vitreous body VB.

Sixth Embodiment

Figure 8A:
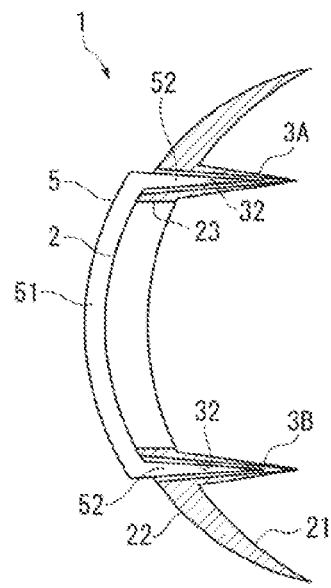
FIGS. 8A and 8B are side elevational views of a medical treatment device according to a sixth embodiment of the present invention.
Figure 8B:
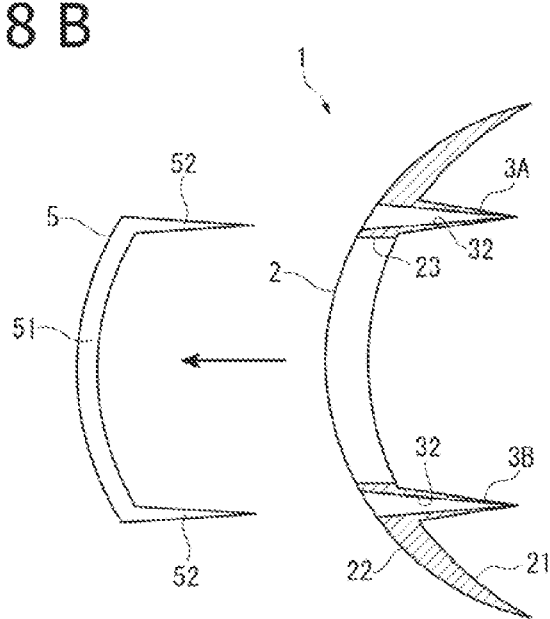

A medical treatment device 1 according to a sixth embodiment of the present invention is different from that of the first embodiment in that the spherical portion 2 and the puncture portions 3A and 3B are different in configuration and that a puncturing member 5 for puncturing the eyeball EB with the puncture portions 3A and 3B is provided as depicted in FIGS. 8A and 8B.

The spherical portion 2 has an opening 23 formed at a central portion thereof. The puncture portions 3A and 3B have a through-hole 32 as an accommodation hole formed so as to extend in the puncture portions 3A and 3B through the spherical portion 2. The through-hole 32 extends through the puncture portions 3A and 3B and the spherical portion 2.

Here, the spherical portion 2 and the puncture portions 3A and 3B are formed from a material softer than that in the first embodiment.

The puncturing member 5 includes a base portion 51 and projections 52 projecting from the base portion 51 and is configured for separation from the spherical portion 2 and the puncture portions 3A and 3B.

The base portion 51 is formed in a spherical shape and has a size sufficient to cover the opening 23 of the spherical portion 2.

The projections 52 are formed similarly in shape and size to the through-holes 32 and are configured for accommodation in the through-holes 32.

Here, the puncturing member 5 is formed from a material harder than that of the spherical portion 2 and the puncture portions 3A and 3B. Therefore, when the medical treatment device 1 is mounted on the eyeball EB, by pushing in the puncturing member 5 in a state in which the projections 52 of the puncturing member 5 are accommodated in the through-holes 32 of the puncture portions 3A and 3B, the puncture portions 3A and 3B puncture the eyeball EB to the angle AN. Thereafter, the puncturing member 5 is separated from the spherical portion 2 and the puncture portions 3A and 3B while the spherical portion 2 and the puncture portions 3A and 3B are indwelled as depicted in FIG. 8B.

With the present embodiment, the following effect is achieved in addition to the effects of the first embodiment.

In particular, because the puncturing member 5 is provided, the spherical portion 2 and the puncture portions 3A and 3B can be formed from a soft material, and an uncomfortable feeling of a patient while the medical treatment device 1 is indwelled can be moderated.

It is to be noted that the present invention is not limited to the embodiments described above, but modifications, improvements and so forth to them within a range within which the object of the present invention can be achieved fall within the scope of the present invention.

Figure 9A:
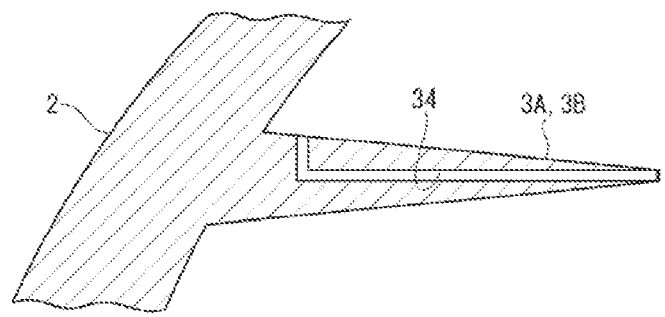
FIGS. 9A and 9B are side elevational views of medical treatment devices according to modifications to certain embodiments of the present invention.
Figure 9B:
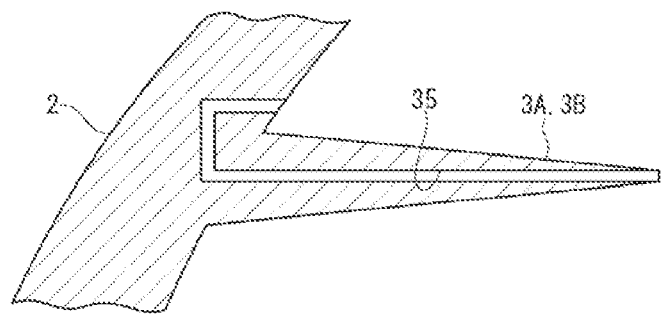

For example, the configuration to be provided on the spherical portion 2 or the puncture portions 3A and 3B in order to discharge the aqueous humor efficiently is not limited to those in the embodiments described hereinabove, but, for example, such a configuration as depicted in FIG. 9A or 9B may be applied. In the puncture portions 3A and 3B depicted in FIG. 9A, a hole 34 is provided in the puncture portions 3A and 3B such that it is open at one end thereof to the distal end of the puncture portions 3A and 3B and is open at the other end thereof to the side face of the puncture portions 3A and 3B. On the other hand, in the spherical portion 2 and the puncture portions 3A and 3B depicted in FIG. 9B, a hole 35 is provided such that it is open at one end thereof to the distal end of the puncture portions 3A and 3B and is open at the other end thereof to the inner side face 21 of the spherical portion 2.

The spherical portion 2 and the puncture portions 3A and 3B may be formed from some other material such as, for example, a resin or a metal if the material has biodegradability. Further, the spherical portion 2 and the puncture portions 3A and 3B may be formed from materials different from each other.

In regards to the puncture portions 3A and 3B, it is necessary to provide at least one puncture portion, and only one puncture portion may be provided or two or more puncture portions may be provided.

Further, the puncture portions 3A and 3B may have such a length that they extend through the iris IR when the medical treatment device 1 is mounted on the eyeball.

Furthermore, the opening of the puncture portions 3A and 3B may be provided at any other portion than the distal end if the aqueous humor can be discharged through the opening.

For the accommodation hole in the puncture portions 3A and 3B, it is only necessary to accommodate the projection 52 of the puncturing member 5 therein and allow the projections 52 to puncture the eyeball EB with the puncture portions 3A and 3B of the projections 52. For example, the accommodation hole may not extend to the distal end of the puncture portions 3A and 3B. Alternatively, an accommodation hole may be provided separately from the through-hole 32.

The puncturing member 5 may have an arbitrary shape such as a spherical shape or an annular shape only if it has the projections 52.

It should be understood by those skilled in the art that various modifications, combinations, sub-combinations and alterations may occur depending on design requirements and other factors insofar as they are within the scope of the appended claims or the equivalents thereof.

What is claimed is:

1. A medical treatment device for treating glaucoma in an eyeball of an individual, comprising:
    a spherical portion formed in a partially spherical shape and configured such that, when the spherical portion is mounted to a front of the eyeball, a concave eyeball side surface of the spherical portion extends along a front surface of the eyeball from an area proximate a top of the front surface of the eyeball to an area proximate a bottom of the front surface of the eyeball; and
    at least one puncture portion protruding from the concave eyeball-side surface of the spherical portion, the at least one puncture portion having a shape of a needle that becomes narrower in a direction away from the concave eyeball-side surface of the spherical portion.

2. The medical treatment device according to claim 1, wherein the at least one puncture portion includes a groove formed thereon extending in a projection direction.

3. The medical treatment device according to claim 1, further comprising a through-hole extending through the at least one puncture portion and the spherical portion.

4. The medical treatment device according to claim 1, wherein the at least one puncture portion comprises a plurality of puncture portions protruding from the concave side of the spherical portion.

5. The medical treatment device according to claim 4, wherein:
the plurality of puncture portions includes at least a first puncture portion and a second puncture portion,
the first puncture portion includes a first opening and the second puncture portion includes a second opening, and
the medical treatment device further comprises a communication passage formed within the spherical portion, the first puncture portion, and the second puncture portion, the communication passage being configured such that the first opening and the second opening communicate with each other.

6. The medical treatment device according to claim 5, wherein:
the first puncture portion has a length sufficient to allow the first puncture portion to extend to at least one of an angle of the eyeball and an iris of the eyeball when the medical treatment device is mounted on the eyeball, and
the second puncture portion has a length sufficient to allow the second puncture portion to extend to a sclera of the eyeball when the medical treatment device is mounted on the eyeball.

7. The medical treatment device according to claim 4, wherein:
the plurality of puncture portions includes at least a first puncture portion and a second puncture portion,
the first puncture portion has a length sufficient to allow the first puncture portion to extend to at least one of an angle of the eyeball and an iris of the eyeball when the medical treatment device is mounted on the eyeball, and
the second puncture portion has a length sufficient to allow the second puncture portion to extend to a vitreous body of the eyeball when the medical treatment device is mounted on the eyeball.

8. The medical treatment device according to claim 7, further comprising an anti-vascular endothelial growth factor agent applied to the second puncture portion.

9. The medical treatment device according to claim 4, wherein:
the plurality of puncture portions includes at least a first puncture portion and a second puncture portion,
the first puncture portion has a length sufficient to allow the first puncture portion to extend to at least one of an angle of the eyeball and an iris of the eyeball when the medical treatment device is mounted on the eyeball, and
the second puncture portion has a length sufficient to allow the second puncture portion to extend to a sclera of the eyeball when the medical treatment device is mounted on the eyeball.

10. The medical treatment device according to claim 1, wherein the spherical portion and the at least one puncture portion comprise a biodegradable material.

11. The medical treatment device according to claim 1, wherein the spherical portion includes an opening formed at a central portion thereof.

12. The medical treatment device according to claim 1, further comprising:
a puncturing member which includes at least one projection configured to cause the at least one puncture portion to puncture the eyeball, and
an accommodation hole extending through the at least one puncture portion and the spherical portion, the accommodation hole being configured to accommodate the at least one projection of the puncturing member therein,
wherein the puncturing member is configured to be separable from the spherical portion and the at least one puncture portion.

13. The medical treatment device according to claim 1, wherein the at least one puncture portion is configured such that, when the medical treatment device is mounted on the eyeball, the at least one puncture portion is provided at a position corresponding to a cornea of the eyeball.

14. The medical treatment device according to claim 1, wherein a length of the at least one puncture portion is sufficient to allow the at least one puncture portion to extend to at least one of an angle of the eyeball and an iris of the eyeball when the medical treatment device is mounted on the eyeball.

15. The medical treatment device according to claim 1, further comprising a gel-like material applied to an outer edge portion of the spherical portion.

16. A method of treating glaucoma in an eyeball of an individual, the method comprising:
providing a medical treatment device comprising:
a spherical portion formed in a partially spherical shape and configured such that, when the spherical portion is mounted to a front of the eyeball, a concave eyeball side surface of the spherical portion extends along a front surface of the eyeball from an area proximate a top of the front surface of the eyeball to an area proximate a bottom of the front surface of the eyeball; and
at least one puncture portion protruding from the concave eyeball-side surface of the spherical portion, the at least one puncture portion having a shape of a needle that becomes narrower in a direction away from the concave eyeball-side surface of the spherical portion; and
mounting the medical treatment device on the front of the eyeball of an individual such that the concave eyeball side surface of the spherical portion extends along a front surface of the eyeball from an area proximate a top of the front surface of the eyeball to an area proximate a bottom of the front surface of the eyeball.

17. The method according to claim 16, wherein the at least one puncture portion is provided at a position corresponding to a cornea of the eyeball.

18. The method according to claim 16, wherein the at least one puncture portion extends to at least one of an angle of the eyeball and an iris of the eyeball.

19. The method according to claim 16, wherein:
the plurality of puncture portions includes at least a first puncture portion and a second puncture portion,
the first puncture portion extends to at least one of an angle of the eyeball and an iris of the eyeball, and
the second puncture portion extends to a vitreous body of the eyeball.

20. The method according to claim 16, wherein:
the plurality of puncture portions includes at least a first puncture portion and a second puncture portion,
the first puncture portion extends to at least one of an angle of the eyeball and an iris of the eyeball, and the second puncture portion extends to a sclera of the eyeball.

\* \* \* \* \*